United States Patent
Tanimoto et al.

(10) Patent No.: US 7,429,678 B2
(45) Date of Patent: Sep. 30, 2008

(54) COMPOSITE-OXIDE CATALYST AND PROCESS FOR PRODUCTION OF ACRYLIC ACID USING SAID CATALYST

(75) Inventors: Michio Tanimoto, Himeji (JP); Harunori Hirao, Himeji (JP)

(73) Assignee: Nippon Shokubai Co., Ltd., Osaka (JP)

(*) Notice: Subject to any disclaimer, the term of this patent is extended or adjusted under 35 U.S.C. 154(b) by 732 days.

(21) Appl. No.: 10/764,852

(22) Filed: Jan. 26, 2004

(65) Prior Publication Data

US 2004/0176641 A1  Sep. 9, 2004

(30) Foreign Application Priority Data

Feb. 27, 2003  (JP) .............................. 2003-051794

(51) Int. Cl.
  *C07C 51/16* (2006.01)
  *C07C 51/235* (2006.01)
(52) U.S. Cl. .................. 562/535; 562/532; 562/534
(58) Field of Classification Search ................ 562/532, 562/544, 534, 535
  See application file for complete search history.

(56) References Cited

U.S. PATENT DOCUMENTS

| | | | |
|---|---|---|---|
| 3,567,773 A | 3/1971 | Yamaguchi et al. | |
| 3,801,634 A | 4/1974 | Krabetz et al. | |
| 4,031,135 A | 6/1977 | Engelbach et al. | |
| RE29,901 E | 2/1979 | Wada et al. | |
| 4,148,757 A | 4/1979 | Brazdil et al. | |
| 4,438,217 A | 3/1984 | Takata et al. | |
| 4,537,874 A | 8/1985 | Sato et al. | |
| 4,769,357 A | 9/1988 | Sarumar et al. | |
| 5,198,580 A | 3/1993 | Bartek et al. | |
| 5,719,318 A | 2/1998 | Kawajiri et al. | |
| 6,492,548 B1* | 12/2002 | Brockwell et al. | 562/545 |
| 6,525,217 B1 | 2/2003 | Unverricht et al. | |
| 6,797,839 B1 | 9/2004 | Hibst et al. | |
| 2002/0065431 A1* | 5/2002 | Chaturvedi et al. | 562/546 |

FOREIGN PATENT DOCUMENTS

| | | |
|---|---|---|
| CA | 1068670 | 12/1979 |
| CN | 1295497 A | 5/2001 |
| CN | 1343194 A | 4/2002 |
| DE | 198 15 278 A1 | 10/1999 |
| EP | 1 055 455 A2 | 11/2000 |
| JP | 44-12129 | 6/1969 |
| JP | 49-11371 | 3/1974 |
| JP | 50-25914 | 8/1975 |
| JP | 51-36415 | 3/1976 |
| JP | 52-85091 | 7/1977 |
| JP | 53-30688 | 8/1978 |
| JP | 55-47144 A | 4/1980 |
| JP | 58-119346 A | 7/1983 |
| JP | 59-76541 A | 5/1984 |
| JP | 63-146841 A | 6/1988 |
| JP | 64-63543 A | 3/1989 |
| JP | 7-10802 A | 1/1995 |
| JP | 8-47641 A | 2/1996 |
| JP | 9-241209 A | 9/1997 |
| JP | 2000-325795 A | 11/2000 |
| JP | 2001-48817 A | 2/2001 |
| JP | 2002/510591 A | 4/2002 |
| JP | 2002-306970 A | 10/2002 |
| WO | WO 99/51341 A1 | 10/1999 |

* cited by examiner

*Primary Examiner*—Yvonne Eyler
*Assistant Examiner*—Jennifer Y Cho

(57) ABSTRACT

There are disclosed a catalyst and a process for production of acrylic acid using this catalyst, wherein, even under conditions where hot spots are formed, the catalyst is excellent in activity, selectivity, and catalyst life time and displays stable performances for a long time. The catalyst is shown by the following formula (1):

$$Mo_aV_bW_cCu_dA_eB_fC_gO_x \qquad (1)$$

Figure 2:
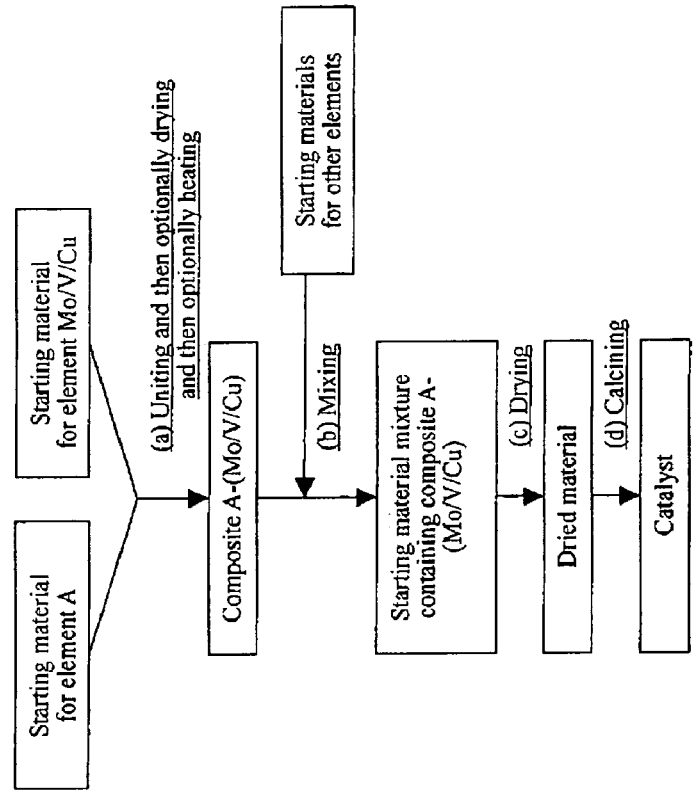
Figure 1:
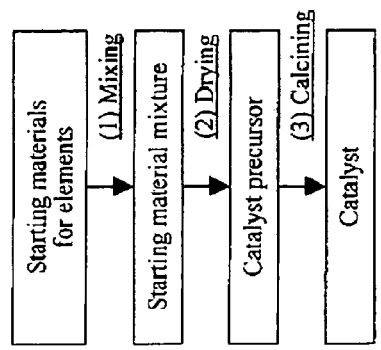

(wherein: A is at least one species selected from among cobalt, nickel, iron, lead, and bismuth; B is at least one species selected from among antimony, niobium, and tin; and C is at least one species selected from among silicon, aluminum, titanium, and zirconium; and further, a, b, c, d, e, f, g, and x are atomic ratios of Mo, V, W, Cu, A, B, C, and O respectively; and, in the case of a=12, the following inequalities are satisfied: $2 \leq b \leq 15$; $0 < c \leq 10$; $0 < d \leq 6$; $0 < e \leq 30$; $0 \leq f \leq 6$; and $0 \leq g \leq 60$; and x is a numerical value as determined by the oxidation state of each element); wherein a supply source of a component A for preparing the catalyst is a composite of the component A and at least one species selected from among Mo, V, and Cu.

3 Claims, 1 Drawing Sheet

Exhibit A

<Present invention>

<Chaturvedi>

COMPOSITE-OXIDE CATALYST AND PROCESS FOR PRODUCTION OF ACRYLIC ACID USING SAID CATALYST

BACKGROUND OF THE INVENTION

A. Technical Field

The present invention relates to: a composite-oxide catalyst used for production of acrylic acid; and a process for production of acrylic acid using this catalyst.

B. Background Art

A large number of catalysts improved for efficiently producing acrylic acid by a catalytic gas phase oxidation reaction of acrolein have hitherto been proposed. For example, there have been disclosed the following catalysts: a catalyst including molybdenum, vanadium, and tungsten (e.g. refer to JP-B-012129/1969); a catalyst including molybdenum, vanadium, copper, tungsten, and chromium (e.g. refer to JP-B-011371/1974); a catalyst including molybdenum and vanadium (e.g. refer to JP-B-025914/1975); and a catalyst including molybdenum, vanadium, copper, and at least one of antimony and germanium (e.g. refer to JP-A-085091/1977).

However, these prior catalysts have a problem such that, when they are used for a long term, their catalytic performances gradually deteriorates due to sublimation of the molybdenum component. And this problem becomes more remarkable due to exposure of the catalysts to high temperature.

As one of means for solution of the above problem, there is disclosed a method for preventing the rise of the hot-spot temperature. For example, there are disclosed the following methods: a method in which a catalyst layer on the raw-gas-inlet side is diluted with an inert substance (e.g. refer to JP-B-030688/1978); and a method in which the supporting ratio of the catalytically active substance is increased in order from the raw-gas-inlet side toward the outlet side (e.g. refer to JP-A-010802/1995).

However, these methods are methods for preventing the hot spots from becoming too high temperature. Therefore, in these methods, the hot spots themselves remain formed as conventional. That is to say, the above methods can never be said to be thorough solutions of the catalytic-performance deterioration caused by the hot spots, and there is accordingly still room for improvement.

On the other hand, when acrylic acid is produced by a catalytic gas phase oxidation reaction of acrolein with a catalyst, usually not a few hot spots are formed in the catalyst, and it is therefore actually difficult to carry out the production with complete elimination of the hot-spot formation.

SUMMARY OF THE INVENTION

A. Object of the Invention

Accordingly, an object of the present invention is to provide a catalyst and a process, wherein, even under conditions where hot spots are formed, the catalyst is excellent in all of activity, selectivity, and catalyst life time and displays stable performances for a long time, and wherein the process produces acrylic acid in a high yield for a long time by a catalytic gas phase oxidation reaction of acrolein with molecular oxygen or a molecular-oxygen-containing gas in the presence of this catalyst.

B. Disclosure of the Invention

The present inventors diligently studied to solve the above problems. As a result, they have found out that a catalyst solving the above problems is a catalyst which is a composite-oxide catalyst including molybdenum, vanadium, tungsten, and copper as essential components and further including at least one element selected from among cobalt, nickel, iron, lead, and bismuth and is prepared in a way that a composite with at least one element selected from among molybdenum, vanadium, and copper is used as a supply source of the aforementioned at least one element selected from among cobalt, nickel, iron, lead, and bismuth. In addition, the present inventors have found out that, if this catalyst is used, then acrylic acid can be produced in a high yield for a long time by a catalytic gas phase oxidation reaction of acrolein with molecular oxygen or a molecular-oxygen-containing gas. Furthermore, by using this catalyst, it has become possible to carry out the application of the catalyst to a high-concentration process which has hitherto been avoided because the catalyst deterioration increases therein.

That is to say, a composite-oxide catalyst, according to the present invention, is a catalyst for production of acrylic acid shown by the following general formula (1):

$$Mo_a V_b W_c Cu_d A_e B_f C_g O_x \qquad (1)$$

(wherein: Mo is molybdenum; V is vanadium; W is tungsten; Cu is copper; A is at least one element selected from among cobalt, nickel, iron, lead, and bismuth; B is at least one element selected from among antimony, niobium, and tin; C is at least one element selected from among silicon, aluminum, titanium, and zirconium; and O is oxygen; and further, a, b, c, d, e, f, g, and x denote atomic ratios of Mo, V, W, Cu, A, B, C, and O respectively; and, in the case of a=12, the following inequalities are satisfied: $2 \leq b \leq 15$; $0 < c \leq 10$; $0 < d \leq 6$; $0 < e \leq 30$; $0 \leq f \leq 6$; and $0 \leq g \leq 60$; and x is a numerical value as determined by the oxidation state of each element);

with the catalyst being characterized in that a supply source of a component A for preparing the catalyst is a composite of the component A and at least one element selected from among molybdenum, vanadium, and copper.

In addition, a process for production of acrylic acid, according to the present invention, is a process comprising the step of carrying out a catalytic gas phase oxidation reaction of acrolein with molecular oxygen or a molecular-oxygen-containing gas, thereby producing the acrylic acid;

with the process being characterized in that the reaction is carried out in the presence of the above composite-oxide catalyst according to the present invention.

Furthermore, another process for production of acrylic acid, according to the present invention, comprises the steps of:

(1) introducing a mixed gas into a first fixed-bed multitubular reactor to thereby produce an acrolein-containing gas, wherein the mixed gas contains high-concentration-propylene and oxygen, but is substantially free from steam, and wherein the first fixed-bed multitubular reactor is packed with a composite-oxide catalyst including molybdenum and bismuth as essential components;

(2) introducing the resultant acrolein-containing gas into a second fixed-bed multitubular reactor to thereby produce an acrylic-acid-containing gas, wherein the second fixed-bed multitubular reactor is packed with a composite-oxide catalyst including molybdenum and vanadium as essential components; and (3) introducing the resultant acrylic-acid-containing gas into an acrylic-acid-absorbing column to thereby collect the acrylic-acid-containing gas as a high-concentration acrylic acid solution;

with the process being characterized in that the above composite-oxide catalyst according to the present invention is used as the composite-oxide catalyst which is packed into the second fixed-bed multitubular reactor; and with the process being further characterized by further comprising the steps of: dividing the inside of each reaction tube of the second fixed-bed multitubular reactor in a tubular axial direction to thereby form at least two reaction zones; and then packing these reaction zones with the above composite-oxide catalysts according to the present invention different as to the amount of the component A in such a manner that the amount of the component A decreases from the gas-inlet side of each reaction tube toward its gas-outlet side.

These and other objects and the advantages of the present invention will be more fully apparent from the following detailed disclosure.

DETAILED DESCRIPTION OF THE INVENTION

The composite-oxide catalyst, according to the present invention, is a catalyst for production of acrylic acid shown by the following general formula (1):

$$Mo_aV_bW_cCu_dA_eB_fC_gO_x \qquad (1)$$

wherein: Mo is molybdenum; V is vanadium; W is tungsten; Cu is copper; A is at least one element selected from among cobalt, nickel, iron, lead, and bismuth; B is at least one element selected from among antimony, niobium, and tin; C is at least one element selected from among silicon, aluminum, titanium, and zirconium; and O is oxygen; and further, a, b, c, d, e, f, g, and x denote atomic ratios of Mo, V, W, Cu, A, B, C, and O respectively; and, in the case of a=12, the following inequalities are satisfied: $2 \leq b \leq 15$; $0 < c \leq 10$; $0 < d \leq 6$; $0 < e \leq 30$; $0 \leq f \leq 6$; and $0 \leq g \leq 60$; and x is a numerical value as determined by the oxidation state of each element.

The composite-oxide catalyst, according to the present invention, is characterized in that a supply source of a component A for preparing the catalyst is a composite of the component A and at least one element selected from among molybdenum, vanadium, and copper. The composite, as referred to hereupon, refers to such as: a material obtained by uniting the starting materials for the elements in an aqueous medium (generally at not higher than 100° C.); a solid (powder) obtained by drying this united material (generally in the range of 100 to 300° C.); and a oxide composite obtained by further treating this solid at higher temperature.

If the component A and the at least one element selected from among molybdenum, vanadium, and copper are beforehand formed into a composite as the supply source of the component A, then there can be obtained the catalyst wherein, even under conditions where hot spots are formed, the catalyst is excellent in all of activity, selectivity, and catalyst life time and displays stable performances for a long time. Its cause, for example, seems to be that the beforehand formation from the component A and the molybdenum into the composite as the supply source of the component A enhances the stability of the molybdenum, and further that the beforehand formation from the component A and the vanadium or copper into the composite also enhances the stability of the molybdenum by exercising some interaction upon the molybdenum.

The process for preparation of the composite-oxide catalyst according to the present invention does essentially not differ from processes as conventionally used for preparation of this type of catalyst, except that, as mentioned above, the component A and the at least one element selected from among molybdenum, vanadium, and copper are beforehand formed into a composite as the supply source of the component A. For example, the process for preparation of the composite-oxide catalyst according to the present invention can be carried out in accordance with any process that has hitherto been well known, such as evaporation-to-dryness process, granulation process, or extrusion molding process.

The shape of the composite-oxide catalyst, according to the present invention, is not especially limited. For example, any shape such as a ring shape, a spherical shape, a column shape, or a tablet shape can be selected. The average diameter of the catalyst, according to the present invention, is favorably in the range of 1 to 15 mm, more favorably 3 to 10 mm. In the above process, there may be added materials which are commonly well known to have effects of improving the strength of the catalyst and decreasing the attrition loss of the catalyst, such as inorganic fibers (e.g. glass fibers) and various whiskers. In addition, for the purpose of controlling the properties of the catalyst with good repeatability, it is also possible to use additives which are commonly known as binders for powders, such as ammonium nitrate, cellulose, starch, polyvinyl alcohol, and stearic acid.

The composite-oxide catalyst, according to the present invention, can be used alone as it is. However, it is also possible to use this catalyst in the form supported on an inert carrier such as alumina, silica-alumina, silicon carbide, titanium oxide, or aluminum sponge. In this case, the supporting ratio (%) (=weight of composite oxide/(weight of inert carrier+weight of composite oxide)×100) of the composite-oxide catalyst shown by the general formula (1) is favorably in the range of 10 to 70%, more favorably 15 to 50%.

There is no especial limitation on the heat-treatment temperature (calcination temperature) during the preparation of the composite-oxide catalyst according to the present invention. However, the targeted composite-oxide catalyst can favorably be obtained by carrying out calcination in the temperature range of 300 to 600° C. (more favorably 350 to 500° C.) for about 1 to about 10 hours.

Because the composite-oxide catalyst according to the present invention is excellent in all of activity, selectivity, and catalyst life time and can display stable performances for a long time, the production of acrylic acid in a high yield for a long time becomes possible by a catalytic gas phase oxidation reaction of acrolein with molecular oxygen or a molecular-oxygen-containing gas in the presence of this catalyst.

That is to say, a process for production of acrylic acid, according to the present invention, is a process comprising the step of carrying out a catalytic gas phase oxidation reaction of acrolein with molecular oxygen or a molecular-oxygen-containing gas, thereby producing the acrylic acid;

with the process being characterized in that the reaction is carried out in the presence of the composite-oxide catalyst according to the present invention.

As the acrolein which is a raw gas in the above production process, a mixed gas containing acrolein as obtained by direct oxidation of propylene is also usable after air or oxygen and further water vapor and/or another gas have been added thereto if necessary, needless to say a mixed gas including acrolein, oxygen, and an inert gas.

There is no especial limitation on such as apparatuses and conditions when the above production process is carried out. That is to say, as to reactors, conventional fixed-bed reactors are used. In addition, as to reaction conditions, the production process can be carried out under conditions as conventionally used for the production of acrylic acid by the catalytic gas phase oxidation reaction. For example, the reaction may be carried out by bringing a mixed gas into contact with the composite-oxide catalyst according to the present invention in the temperature range of 200 to 400° C. (favorably 220 to 380° C.) under a pressure of 0.1 to 1 MPa at a space velocity of 300 to 10,000 $hr_{-1}$ (STP) (favorably 500 to 5,000 $hr^{-1}$ (STP)), wherein the mixed gas includes such as acrolein 1 to 15 volume % (favorably 4 to 12 volume %), oxygen 0.5 to 25 volume % (favorably 2 to 20 volume %), water vapor 1 to 30 volume % (favorably 3 to 20 volume %), and an inert gas (e.g. nitrogen) 20 to 80 volume % (favorably 50 to 70 volume %).

Furthermore, because, even under conditions where hot spots are formed, the composite-oxide catalyst according to the present invention is excellent in all of activity, selectivity, and catalyst life time and can display stable performances for a long time, it has become possible to carry out the application of the catalyst to a high-concentration process which has hitherto been avoided because the catalyst deterioration increases therein.

That is to say, another process for production of acrylic acid, according to the present invention, comprises the steps of:

(1) introducing a mixed gas into a first fixed-bed multitubular reactor to thereby produce an acrolein-containing gas, wherein the mixed gas contains high-concentration-propylene and oxygen, but is substantially free from steam, and wherein the first fixed-bed multitubular reactor is packed with a composite-oxide catalyst including molybdenum and bismuth as essential components;

(2) introducing the resultant acrolein-containing gas into a second fixed-bed multitubular reactor to thereby produce an acrylic-acid-containing gas, wherein the second fixed-bed multitubular reactor is packed with a composite-oxide catalyst including molybdenum and vanadium as essential components; and (3) introducing the resultant acrylic-acid-containing gas into an acrylic-acid-absorbing column to thereby collect the acrylic-acid-containing gas as a high-concentration acrylic acid solution;

with the process being characterized in that the composite-oxide catalyst according to the present invention is used as the composite-oxide catalyst which is packed into the second fixed-bed multitubular reactor; and with the process being further characterized by further comprising the steps of: dividing the inside of each reaction tube of the second fixed-bed multitubular reactor in a tubular axial direction to thereby form at least two reaction zones; and then packing these reaction zones with the composite-oxide catalysts according to the present invention different as to the amount of the component A in such a manner that the amount of the component A decreases from the gas-inlet side of each reaction tube toward its gas-outlet side.

The above production process comprises the steps of: (1) producing an acrolein-containing gas; (2) producing an acrylic-acid-containing gas from the acrolein-containing gas resultant from the step (1) ; and (3) introducing the acrylic-acid-containing gas, resultant from the step (2), into an acrylic-acid-absorbing column to thereby collect the acrylic-acid-containing gas as a high-concentration acrylic acid solution.

The raw gas, as used in the step (1), contains propylene in a high concentration. The high concentration, as referred to hereupon, means that the propylene concentration in the raw gas is favorably not less than 7 volume %, more favorably in the range of 8 to 20 volume %, still more favorably 9 to 15 volume %. Making the propylene concentration high to such a degree increases the productivity of acrylic acid.

On the other hand, in the case where the propylene concentration in the raw gas is increased, the amount of the load to the catalyst increases to accelerate the deterioration of the catalyst more than conventional. Particularly as to conventional catalysts including molybdenum and vanadium as essential components, there have been problems in that the deterioration is so great that acrylic acid cannot be produced stably for a long time. However, it has been found out that the above problems can be solved by adopting the process in which: the composite-oxide catalyst according to the present invention is used as the composite-oxide catalyst which is packed into the second fixed-bed multitubular reactor; and further, the inside of each reaction tube of the second fixed-bed multitubular reactor is divided in a tubular axial direction to thereby form at least two reaction zones; and then these reaction zones are packed with the composite-oxide catalysts according to the present invention different as to the amount of the component A in such a manner that the amount of the component A decreases from the gas-inlet side of each reaction tube toward its gas-outlet side.

The raw gas, as used in the step (1), further contains oxygen. The volume ratio between propylene and oxygen (propylene:oxygen) in the raw gas is favorably in the range of 1:1-2.5, more favorably 1:1.05-2.2, still more favorably 1:1.1-2.0.

The raw gas, as used in the step (1), may contain a saturated hydrocarbon which is substantially inert in the catalytic gas phase oxidation reaction of propylene (in other words, does substantially not undergo the oxidation reaction). Examples of such a saturated hydrocarbon include methane, ethane, propane, and butane. The main purpose for which such a saturated hydrocarbon is added to the raw gas is a role as a balance gas and further a role as a component substituted for steam which is conventionally used as an inert diluting gas. The volume ratio of the balance gas (including the inert saturated hydrocarbon) to propylene (saturated hydrocarbon/propylene) is favorably in the range of 0-1.5.

The raw gas, as used in the step (1), is substantially free from steam. This means that no steam is intentionally (positively) added to the raw gas as used in the step (1) . Accordingly, water (moisture) in the atmosphere, which is contained in the case where the supply source of the molecular oxygen, particularly, air, is used, does not correspond to the steam as referred to hereupon.

Because substantially no steam is contained in the raw gas as used in the step (1), the high-concentration acrylic acid solution can be obtained. As a result, the energy consumption done by such as steam in the step for purification of acrylic acid can be reduced. In addition, the amount of water as discharged out of the system can be reduced.

As to the concentration of the above steam, 0 volume % is the most favorable for increasing the acrylic acid concentration in the acrylic-acid-absorbing column. However, the present invention is tolerant of the steam concentration which is determined from the humidity and temperature in the atmosphere. Examples of favorable modes include a mode in which such as air, which is a supply source of the molecular oxygen, is introduced into an apparatus having a dehumidifying function and thereby used as a molecular-oxygen supply source that is not affected by the humidity or temperature.

In addition, if the steam concentration decreases, problems have occurred to conventional catalysts including molybdenum and vanadium as essential components, in that the deterioration is so great that acrylic acid cannot be produced stably for a long time. However, as is aforementioned, the solution of the above problems has become possible by adopting the process in which: the composite-oxide catalyst according to the present invention is used as the composite-oxide catalyst which is packed into the second fixed-bed multitubular reactor; and further, the inside of each reaction tube of the second fixed-bed multitubular reactor is divided in a tubular axial direction to thereby form at least two reaction zones; and then these reaction zones are packed with the composite-oxide catalysts according to the present invention different as to the amount of the component A in such a manner that the amount of the component A decreases from the gas-inlet side of each reaction tube toward its gas-outlet side.

The composite-oxide catalyst including molybdenum and bismuth as essential components, which is packed into the first fixed-bed multitubular reactor, is not especially limited. However, hitherto publicly known composite-oxide catalysts including molybdenum and bismuth as essential components can be used. Specific examples of the usable catalysts include those which are disclosed in JP-A-119346/1983, JP-A-076541/1984, and JP-A-325795/2000.

As to the reaction gas to be supplied to the step (2), a gas flowing out of the first fixed-bed multitubular reactor can be used as it is. However, as the case may be, it is also possible that: the gas flowing out of the first fixed-bed multitubular reactor is mixed with a molecular-oxygen-containing gas, and then the resultant mixture is introduced into the second fixed-bed multitubular reactor. In this case, as to the concentration of the oxygen to be added, the molecular-oxygen-containing gas is added in such an amount that the "propylene:oxygen" (volume ratio) can be favorably in the range of 1:1.5-3.5, more favorably 1:1.55-3.0, still more favorably 1:1.6-2.5, in the total of a reaction gas which is supplied into the first fixed-bed multitubular reactor and the molecular-oxygen-containing gas which is added to the gas flowing out of the first fixed-bed multitubular reactor.

In the step (2), the composite-oxide catalyst according to the present invention is used as the composite-oxide catalyst which is packed into the second fixed-bed multitubular reactor. By this use of the composite-oxide catalyst according to the present invention, the deterioration of the catalyst can be inhibited and therefore acrylic acid can be produced stably for a long time, even if the propylene concentration in the raw gas which is introduced into the first reactor is increased or even if the raw gas is made substantially free from steam.

In addition, in the step (2), the inside of each reaction tube of the second fixed-bed multitubular reactor is divided in a tubular axial direction to thereby form at least two reaction zones; and then these reaction zones are packed with the composite-oxide catalysts according to the present invention different as to the amount of the component A in such a manner that the amount of the component A decreases from the gas-inlet side of each reaction tube toward its gas-outlet side. By making such a constitution, the sublimation of the molybdenum can be inhibited even if a hot-spot portion occurs. Therefore, the deterioration of the catalyst can be inhibited and therefore acrylic acid can be produced stably for a long time, even if the propylene concentration in the raw gas is increased or even if the raw gas is made substantially free from steam.

There is no especial limitation on the number of the reaction zones formed by dividing the inside of each reaction tube of the second fixed-bed multitubular reactor in a tubular axial direction. However, in the case where the number of the reaction zones is too large, there newly occur problems such that the operation of packing the catalyst is complicated. Therefore, industrially, the purposed effects can be obtained sufficiently by adjusting the number favorably to about 2 to about 6, more favorably to about 2 or about 3. In addition, as to the ratio between the divided catalyst layers, its optimum value depends upon such as: oxidation reaction conditions; and composition, shape, and size of the catalyst as packed in each layer. Therefore, the ratio cannot be specified sweepingly. The ratio may appropriately be selected so as to obtain the optimum activity and selectivity as a whole.

When each reaction tube of the second fixed-bed multitubular reactor is packed with the composite-oxide catalysts, it is also possible to use not only the above packing method, but also this method in combination with hitherto publicly known packing methods such as: a method in which, when the reaction tube is packed with at least two kinds of catalysts, the packing is carried out in such a manner that the volume of the catalyst decreases from the raw-gas-inlet side toward the outlet side (JP-A-241209/1997); a method in which the reaction tube is packed with catalysts in such a manner that the supporting ratio of the catalytically active substance increases in order from the raw-gas-inlet side of the reaction tube toward its outlet side (JP-A-010802/1995); and a method in which a catalyst on the raw-gas-inlet side is diluted with an inert substance (JP-B-030688/1978).

(Effects and Advantages of the Invention):

The present invention can provide a catalyst and a process, wherein, even under conditions where hot spots are formed, the catalyst is excellent in all of activity, selectivity, and catalyst life time and displays stable performances for a long time, and wherein the process produces acrylic acid in a high yield for a long time by a catalytic gas phase oxidation reaction of acrolein with molecular oxygen or a molecular-oxygen-containing gas in the presence of this catalyst. In addition, by using the catalyst according to the present invention, it becomes possible to carry out the application of the catalyst to a high-concentration process which has hitherto been avoided because the catalyst deterioration increases therein.

DETAILED DESCRIPTION OF THE PREFERRED EMBODIMENTS

Hereinafter, the present invention is more specifically illustrated by the following Examples of some preferred embodiments in comparison with Comparative Examples not according to the present invention. However, the present invention is not limited to these Examples in any way.

Incidentally, the conversion of acrolein, the selectivity of acrylic acid, and the yield of acrylic acid were determined by the following equations.

Conversion of acrolein (mol %)=(mols of reacted acrolein)/(mols of supplied acrolein)×100

Selectivity of acrylic acid (mol %)=(mols of produced acrylic acid)/(mols of reacted acrolein)×100

Yield of acrylic acid (mol %)=(mols of produced acrylic acid)/(mols of supplied acrolein)×100

EXAMPLE 1

(Preparation of Fe—Mo Precursor):

While 500 mL of pure water was heat-stirred, 21.9 g of ammonium paramolybdate was dissolved thereinto. Separately, while 150 mL of pure water was heat-stirred, 33.4 g of ferric nitrate was dissolved thereinto. The resultant two liquids were mixed together. Thereafter, while stirred, the resultant mixture was retained at a temperature of 80° C. for 1 hour, and then water was removed therefrom, and then the residue was heat-treated at 500° C. for 3 hours. The resultant solid was pulverized so as to have particle diameters of not larger than 100 µm, thus preparing the Fe—Mo precursor.

(Preparation of Catalyst):

While 2,000 mL of pure water was heat-stirred, 328 g of ammonium paramolybdate, 96.6 g of ammonium metavanadate, and 53.5 g of ammonium paratungstate were dissolved thereinto. Separately, while 200 g of pure water was heat-stirred, 79.8 g of cupric nitrate and 4.8 g of antimony trioxide were added thereinto. The resultant two liquids were mixed together, and then the Fe—Mo precursor as beforehand prepared above was added to the resultant mixture. The resultant mixture was placed into a porcelain evaporator on a hot water bath, and then 1,200 mL of a silica-alumina-made spherical carrier of 5 mm in average particle diameter was added thereto. While stirred, the resultant mixture was evaporated to dryness to thereby carry out the attachment to the carrier. The resultant material was calcined at 400° C. for 6 hours, thus preparing a catalyst (1). The metal element composition of this catalyst (1) (except for oxygen, hereinafter the same) was as follows.

$Mo_{12}V_5W_{1.2}Cu_2Sb_{0.2}Fe_{0.5}$ <span style="float:right">Catalyst (1)</span>

(Durability Test):

An amount of 200 mL of the catalyst (1), as obtained in the above way, was packed into a stainless-steel-made reaction tube of 25 mm in inner diameter and 800 mm in length as equipped with a heating-medium jacket. Thereafter, a reaction was carried out for 2,000 hours under conditions of contact time=1.5 seconds by introducing a mixed gas, including acrolein 4 volume %, air 20 volume %, and water vapor 76 volume %, into the above reaction tube. During this reaction, the reaction temperature was adjusted so that the conversion of acrolein could be maintained in the range of 98 to 99 mol %.

After the end of the reaction, the catalyst as extracted from the reaction tube was uniformly mixed and then pulverized so as to have particle diameters of not larger than 50 µm. An amount of 5 g of powder was precisely weighed out, and then molded under pressure (20 tons), and then subjected to fluorescent X-ray analysis (measurement conditions: Rh tube, 50 kV, 50 mA, measurement instrument: RIX2000 produced by Rigaku Denki Kogyo K.K.).

The catalyst which had not been used for the reaction (unused catalyst) was also subjected to the same fluorescent X-ray analysis. When assuming that the peak intensity of molybdenum in the unused catalyst was 100, the peak intensity of molybdenum in the catalyst which had been used for the reaction for 2,000 hours (used catalyst) was 90.

COMPARATIVE EXAMPLE 1

(Preparation of Catalyst):

In Example 1, a catalyst was prepared in accordance with the following procedure without beforehand carrying out the preparation of the Fe-Mo precursor.

While 2,000 mL of pure water was heat-stirred, 350 g of ammonium paramolybdate, 96.6 g of ammonium metavanadate, and 53.5 g of ammonium paratungstate were dissolved thereinto. Separately, while 200 g of pure water was heat-stirred, 79.8 g of cupric nitrate, 33.4 g of ferric nitrate, and 4.8 g of antimony trioxide were added thereinto. The resultant two liquids were mixed together, and then the resultant mixture was placed into a porcelain evaporator on a hot water bath, and then 1,200 mL of a silica-alumina-made spherical carrier of 5 mm in average particle diameter was added thereto. While stirred, the resultant mixture was evaporated to dryness to thereby carry out the attachment to the carrier. The resultant material was calcined at 400° C. for 6 hours, thus preparing a comparative catalyst (c1) having the same composition as of the catalyst (1).

(Durability Test):

The reaction and the fluorescent X-ray analysis were carried out in the same way as of Example 1 except that the catalyst (1) was replaced with the comparative catalyst (c1). As a result, when assuming that the peak intensity of molybdenum in the unused catalyst was 100, the peak intensity of molybdenum in the used catalyst was 78.

EXAMPLE 2

(Preparation of Fe—Mo Precursor):

While 500 mL of pure water was heat-stirred, 87.5 g of ammonium paramolybdate was dissolved thereinto. Separately, while 150 mL of pure water was heat-stirred, 133 g of ferric nitrate was dissolved thereinto. The resultant two liquids were mixed together. Thereafter, while stirred, the resultant mixture was retained at a temperature of 80° C. for 1 hour, and then water was removed therefrom, and then the residue was heat-treated at 500° C. for 3 hours. The resultant solid was pulverized so as to have particle diameters of not larger than 100 µm, thus preparing the Fe—Mo precursor.

(Preparation of Catalyst):

While 2,000 mL of pure water was heat-stirred, 262.5 g of ammonium paramolybdate, 96.6 g of ammonium metavanadate, and 53.5 g of ammonium paratungstate were dissolved thereinto. Separately, while 200 g of pure water was heat-stirred, 79.8 g of cupric nitrate and 4.8 g of antimony trioxide were added thereinto. The resultant two liquids were mixed together, and then the Fe—Mo precursor as beforehand prepared above was added to the resultant mixture. The resultant mixture was placed into a porcelain evaporator on a hot water bath, and then 1,200 mL of a silica-alumina-made spherical carrier of 5 mm in average particle diameter was added thereto. While stirred, the resultant mixture was evaporated to dryness to thereby carry out the attachment to the carrier. The resultant material was calcined at 400° C. for 6 hours, thus preparing a catalyst (2). The metal element composition of this catalyst (2) was as follows.

$Mo_{12}V_5W_{1.2}Cu_2Sb_{0.2}Fe_2$ <span style="float:right">Catalyst (2)</span>

(Durability Test):

The reaction and the fluorescent X-ray analysis were carried out in the same way as of Example 1 except that the catalyst (1) was replaced with the catalyst (2). As a result, when assuming that the peak intensity of molybdenum in the unused catalyst was 100, the peak intensity of molybdenum in the used catalyst was 95.

COMPARATIVE EXAMPLE 2

(Preparation of Catalyst):

In Example 2, a catalyst was prepared in accordance with the following procedure without beforehand carrying out the preparation of the Fe—Mo precursor.

While 2,000 mL of pure water was heat-stirred, 350 g of ammonium paramolybdate, 96.6 g of ammonium metavanadate, and 53.5 g of ammonium paratungstate were dissolved thereinto. Separately, while 200 g of pure water was heat-stirred, 79.8 g of cupric nitrate, 133 g of ferric nitrate, and 4.8 g of antimony trioxide were added thereinto. The resultant two liquids were mixed together, and then the resultant mixture was placed into a porcelain evaporator on a hot water bath, and then 1,200 mL of a silica-alumina-made spherical carrier of 5 mm in average particle diameter was added thereto. While stirred, the resultant mixture was evaporated to dryness to thereby carry out the attachment to the carrier. The resultant material was calcined at 400° C. for 6 hours, thus preparing a comparative catalyst (c2) having the same composition as of the catalyst (2).

(Durability Test):

The reaction and the fluorescent X-ray analysis were carried out in the same way as of Example 1 except that the catalyst (1) was replaced with the comparative catalyst (c2). As a result, when assuming that the peak intensity of molybdenum in the unused catalyst was 100, the peak intensity of molybdenum in the used catalyst was 80.

EXAMPLE 3

(Preparation of Fe—Cu—V Precursor):

While 500 mL of pure water was heat-stirred, 20 g of cupric nitrate and 19.3 g of ammonium metavanadate were dissolved thereinto. Separately, while 150 mL of pure water was heat-stirred, 33.4 g of ferric nitrate was dissolved thereinto. The resultant two liquids were mixed together. Thereafter, while stirred, the resultant mixture was retained at a temperature of 80° C. for 1 hour, and then water was removed therefrom, and then the residue was heat-treated at 200° C. for 5 hours. The resultant solid was pulverized so as to have particle diameters of not larger than 100 μm, thus preparing the Fe—Cu—V precursor.

(Preparation of Catalyst):

While 2,000 mL of pure water was heat-stirred, 350 g of ammonium paramolybdate, 77.3 g of ammonium metavanadate, and 53.5 g of ammonium paratungstate were dissolved thereinto. Separately, while 200 g of pure water was heat-stirred, 60 g of cupric nitrate and 4.8 g of antimony trioxide were added thereinto. The resultant two liquids were mixed together, and then the Fe—Cu—V precursor as beforehand prepared above was added to the resultant mixture. The resultant mixture was placed into a porcelain evaporator on a hot water bath, and then 1,200 mL of a silica-alumina-made spherical carrier of 5 mm in average particle diameter was added thereto. While stirred, the resultant mixture was evaporated to dryness to thereby carry out the attachment to the carrier. The resultant material was calcined at 400° C. for 6 hours, thus preparing a catalyst (3). The metal element composition of this catalyst (3) was as follows.

$$Mo_{12}V_5W_{1.2}Cu_2Sb_{0.2}Fe0.5 \qquad \text{Catalyst (3)}$$

(Durability Test):

The reaction and the fluorescent X-ray analysis were carried out in the same way as of Example 1 except that the catalyst (1) was replaced with the catalyst (3). As a result, when assuming that the peak intensity of molybdenum in the unused catalyst was 100, the peak intensity of molybdenum in the used catalyst was 92.

EXAMPLE 4

(Preparation of Bi—Mo Precursor):

While 500 mL of pure water was heat-stirred, 43.8 g of ammonium paramolybdate was dissolved thereinto. Separately, while a mixed liquid of 150 mL of pure water and 30 g of 65 mass % nitric acid was heat-stirred, 80 g of bismuth nitrate was dissolved thereinto. The resultant two liquids were mixed together. Thereafter, while stirred, the resultant mixture was retained at a temperature of 80° C. for 1 hour, and then water was removed therefrom, and then the residue was heat-treated at 400° C. for 3 hours. The resultant solid was pulverized so as to have particle diameters of not larger than 100 μm, thus preparing the Bi-Mo precursor.

(Preparation of Catalyst):

While 2,000 mL of pure water was heat-stirred, 306 g of ammonium paramolybdate, 87.0 g of ammonium metavanadate, and 66.9 g of ammonium paratungstate were dissolved thereinto. Separately, while 200 g of pure water was heat-stirred, 79.8 g of cupric nitrate and 4.8 g of antimony trioxide were added thereinto. The resultant two liquids were mixed together, and then the Bi—Mo precursor as beforehand prepared above was added to the resultant mixture. The resultant mixture was placed into a porcelain evaporator on a hot water bath, and then 1,200 mL of a silica-alumina-made spherical carrier of 5 mm in average particle diameter was added thereto. While stirred, the resultant mixture was evaporated to dryness to thereby carry out the attachment to the carrier. The resultant material was calcined at 400° C. for 6 hours, thus preparing a catalyst (4). The metal element composition of this catalyst (4) was as follows.

$$Mo_{12}V_{4.5}W_{1.5}Cu_2Bi_1 \qquad \text{Catalyst (4)}$$

(Durability Test):

The reaction and the fluorescent X-ray analysis were carried out in the same way as of Example 1 except that the catalyst (1) was replaced with the catalyst (4). As a result, when assuming that the peak intensity of molybdenum in the unused catalyst was 100, the peak intensity of molybdenum in the used catalyst was 89.

EXAMPLE 5

(Preparation of Catalyst):

A catalyst (5) was prepared in the same way as of Example 1 except that a silica-alumina-made spherical carrier of 8 mm in average particle diameter was used when the catalyst was prepared.

(Oxidation Reaction):

(Process as Disclosed in JP-A-241209/1997):

A reaction tube of 25 mm in inner diameter and 3,500 mm in length, as equipped with a jacket for heating-medium circulation, was packed with ① the catalyst (5) and ② the catalyst (1) so that their packed-layer lengths would be 1,000 mm and 2,000 mm respectively in that order from the gas-inlet side of the reaction tube toward its gas-outlet side.

A mixed gas, including acrolein 5.5 volume %, oxygen 6 volume %, water vapor 25 volume %, and inert gas (including such as nitrogen) 63.5 volume %, was introduced into the above reactor under conditions of contact time=2 seconds to continue the reaction for 8,000 hours. This reaction was continued while the heating-medium temperature was adjusted so as to give a conversion of acrolein of 98.5±0.5 mol % under an outlet pressure of 0.15 MPa (absolute pressure) of the reactor. Incidentally, 100 hours later than the initiation of the reaction, the heating-medium temperature was 262° C., and the yield of acrylic acid was 94.2 mol %. In addition, at a passage of 8,000 hours from the initiation of the reaction, the heating-medium temperature was 270° C., and the yield of acrylic acid was 93.8 mol %.

COMPARATIVE EXAMPLE 3

(Preparation of Catalyst):
A comparative catalyst (c3) was prepared in the same way as of Comparative Example 1 except that a silica-alumina-made spherical carrier of 8 mm in average particle diameter was used when the catalyst was prepared.

(Oxidation Reaction):
The reaction was carried out in the same way as of Example 5 except that the catalyst (5) was replaced with the comparative catalyst (c3), and that the catalyst (1) was replaced with the comparative catalyst (c1). As a result, 100 hours later than the initiation of the reaction, the heating-medium temperature was 264° C., and the yield of acrylic acid was 93.1 mol %. In addition, at a passage of 8,000 hours from the initiation of the reaction, the heating-medium temperature was 279° C., and the yield of acrylic acid was 92.5 mol %.

EXAMPLE 6

(Preparation of Mo—Bi Catalyst):
A molybdenum-bismuth catalyst (6a) was prepared according to the teachings of Example 1 as disclosed in JP-A-325795/2000.

(Preparation of Mo—V Catalyst):
A molybdenum-vanadium catalyst (6b) was prepared in the same way as of Example 2 except that a silica-alumina-made spherical carrier of 8 mm in average particle diameter was used when the catalyst was prepared.

(Oxidation Reaction):
There was prepared a reactor having a reaction tube which was 25 mm in inner diameter and 7,000 mm in length and was equipped with a jacket for heating-medium circulation, wherein a 75-mm-thick partition dividing the heating-medium jacket into upper and lower portions was placed in a position of 3,500 mm above the lower end of the jacket, so that each of the divided upper and lower heating-media could be circulated to control their respective temperatures (wherein: the lower portion corresponded to the first reactor, and the upper portion corresponded to the second reactor). Then, the above reaction tube was packed with ① ceramic balls only, ② a mixture of 70:30 in volume ratio of the catalyst (6a) and the ceramic balls, ③ the catalyst (6a) only, ④ a stainless-steel-made Raschig ring of 6.5 mm in outer diameter, 6 mm in inner diameter and 6.5 mm in length, ⑤ the catalyst (6b), and ⑥ the catalyst (1) so that their packed-layer lengths would be 300 mm, 800 mm, 2,200 mm, 500 mm, 700 mm, and 2,300 mm respectively in that order from the lower portion of the reaction tube toward its upper portion.

Into the first reactor, there were introduced the following: propylene of 96 volume % in purity (with the balance being mainly propane) at a rate of 219 L (normal)/hour; air of 20° C. in temperature and 80 volume % in relative humidity at a rate of 1,838 L (normal)/hour; and inert saturated hydrocarbon (mainly, methane) other than propane from the above raw propylene at a rate of 152 L (normal)/hour. In this step, the reaction was continued while the respective heating-medium temperatures of the first and second reactors were adjusted so as to give a conversion of propylene of 98±0.5 mol % and a yield of acrolein of 1±0.5 mol % under an outlet pressure of 0.15 MPa (absolute pressure) of the second reactor. In Table 1, there is shown a reaction duration at the attainment to a reaction temperature of 300° C. Incidentally, 100 hours later than the initiation of the reaction, the yield of acrylic acid was 88 mol %. In addition, when the amount of water being absorbed was adjusted so that the acrylic acid absorption efficiency would be 99.5 mass % when the acrylic-acid-absorbing column had a column-top temperature of 62.5° C. and a column-top pressure of 11 kPa-G, then the concentration of the acrylic acid solution was 79.7 mass %.

COMPARATIVE EXAMPLE 4

(Preparation of Catalyst):
A comparative catalyst (c4) was prepared in the same way as of Comparative Example 2 except that a silica-alumina-made spherical carrier of 8 mm in average particle diameter was used when the catalyst was prepared.

(Oxidation Reaction):
The reaction was carried out in the same way as of Example 6 except that the catalyst (6b) was replaced with the comparative catalyst (c4), and that the catalyst (1) was replaced with the comparative catalyst (c1). In Table 1, there is shown a reaction duration at the attainment to a reaction temperature of 300° C. Incidentally, 100 hours later than the initiation of the reaction, the yield of acrylic acid was 85.8 mol %. In addition, when the amount of water being absorbed was adjusted so that the acrylic acid absorption efficiency would be 99.5 mass % when the acrylic-acid-absorbing column had a column-top temperature of 62.5° C. and a column-top pressure of 11 kPa-G, then the concentration of the acrylic acid solution was 75.8 mass %.

TABLE 1

| | Reaction temperature at initiation of reaction | Reaction duration at attainment to 300° C. |
|---|---|---|
| Example 6 | 265° C. | 24,000 Hrs |
| Comparative Example 4 | 268° C. | 13,000 Hrs |

EXAMPLE 7

(Oxidation Reaction):
There was prepared a reaction apparatus having a series of two reaction tubes of 25 mm in inner diameter and 3,500 mm in length as equipped with a jacket for heating-medium circulation wherein the reaction tubes were connected to each other's one end through piping wherein a nozzle was equipped to the piping which connected the outlet of the first reactor and the inlet of the second reactor. Then, the first reactor was packed with ① a mixture of 50:50 in volume ratio of the catalyst (6a) and a diluent (ceramic balls), ② a mixture of 70:30 in volume ratio of the catalyst (6a) and the diluent, and ③ the catalyst (6a) so that their packed-layer lengths would be 500 mm, 500 mm, and 2,000 mm respectively in that order from the gas-inlet side of the first reactor toward its gas-outlet side.

The second reactor was packed with ① the catalyst (6b) and the catalyst (1) so that their packed-layer lengths would be 700 mm and 2,000 mm respectively in that order from the gas-inlet side of the second reactor toward its gas-outlet side.

Into the first reactor, there were introduced the following: propylene of 96 volume % in purity (with the balance being mainly propane) at a rate of 249 L (normal)/hour and air of 20° C. in temperature and 80 volume % in relative humidity at a rate of 1,741 L (normal)/hour. Air of 20° C. in temperature and 80 volume % in relative humidity was introduced at a rate of 492 L (normal)/hour from a nozzle as equipped to the piping which connected the outlet of the first reactor and the inlet of the second reactor:

In this step, the reaction was continued while the respective heating-medium temperatures of the first and second reactors were adjusted so as to give a conversion of propylene of 98±0.5 mol % and a yield of acrolein of 1±0.5 mol % under an outlet pressure of 0.15 MPa (absolute pressure) of the second reactor. Incidentally, 100 hours later than the initiation of the reaction, the yield of acrylic acid was 87.2 mol %. In addition, when the amount of water being absorbed was adjusted so that the acrylic acid absorption efficiency would be 99.5 mass % when the acrylic-acid-absorbing column had a column-top temperature of 62.5 ° C and a column-top pressure of 11 kPa-G, then the concentration of the acrylic acid solution was 78.7 mass %.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A process for production of acrylic acid, which is a process comprising the step of carrying out a catalytic gas phase oxidation reaction of acrolein with molecular oxygen or a molecular-oxygen-containing gas, thereby producing the acrylic acid;

wherein the reaction is carried out in the presence of a composite-oxide catalyst shown by the following general formula (1):

$$Mo_a V_b W_c Cu_d A_e B_f C_g O_x \quad (1)$$

(wherein: Mo is molybdenum; V is vanadium; W is tungsten; Cu is copper; A is at least one element selected from among cobalt, nickel, iron, lead, and bismuth; B is at least one element selected from among antimony, niobium, and tin; C is at least one element selected from among silicon, aluminum, titanium, and zirconium; and O is oxygen; and further, a, b, c, d, e, f, g, and x denote atomic ratios of Mo, V, W, Cu, A, B, C, and O respectively; and, in the case of a =12, the following inequalities are satisfied: $2 \leq b \leq 15$; $0 < c \leq 10$; $0 < d \leq 6$; $0 < e \leq 30$; $0 \leq f \leq 6$; and $0 \leq g \leq 60$; and x is a numerical value as determined by the oxidation state of each element);

wherein said composite-oxide catalyst is prepared by the steps of:
a) uniting a starting material for element A with a starting material selected from among molybdenum, vanadium, and copper to form a united material, then optionally drying said united material and optionally heating said dried material, such that a composite A is obtained;
b) mixing said composite A and starting materials for other elements to obtain a starting material mixture containing said composite A;
c) drying said starting material mixture containing said composite A to obtain a dried material containing said composite A; and
d) calcining said dried material containing said composite A to obtain said composite-oxide catalyst.

2. A process for production of acrylic acid according to claim 1, which comprises the steps of:
(1) introducing a mixed gas into a first fixed-bed multitubular reactor to thereby produce an acrolein-containing gas, wherein the mixed gas contains high-concentration-propylene and oxygen, but is substantially free from steam, and wherein the first fixed-bed multitubular reactor is packed with a composite-oxide catalyst including molybdenum and bismuth as essential components;
(2) introducing the resultant acrolein-containing gas into a second fixed-bed multitubular reactor to thereby produce an acrylic-acid-containing gas, wherein the second fixed-bed multitubular reactor is packed with a composite-oxide catalyst including molybdenum and vanadium as essential components; and
(3) introducing the resultant acrylic-acid-containing gas into an acrylic-acid-absorbing column to thereby collect the acrylic-acid-containing gas as a high-concentration acrylic acid solution;
wherein the composite-oxide catalyst as recited in claim is used as the composite-oxide catalyst which is packed into the second fixed-bed multitubular reactor; and
with the process further comprising the steps of: dividing the inside of each reaction tube of the second fixed-bed multitubular reactor in a tubular axial direction to thereby form at least two reaction zones; and then packing these reaction zones which the composite-oxide catalysts as recited in claim 2 different as to the amount of element A in such a manner that the amount of element A decreases from the gas-inlet side of each reaction tube toward its gas-outlet side.

3. A process for production of acrylic acid according to claim 2, wherein the mixed gas which is introduced into the first fixed-bed muititubular reactor further contains a saturated hydrocarbon which does substantially not react by oxidation in this reactor.

* * * * *